United States Patent [19]

Lee

[11] 4,201,567
[45] May 6, 1980

[54] HERBICIDAL PYRIDINE, 1-OXIDES

[75] Inventor: Kyu T. Lee, Wilmington, Del.

[73] Assignee: E. I. Du Pont de Nemours and Company, Wilmington, Del.

[21] Appl. No.: 4,918

[22] Filed: Jan. 19, 1979

[51] Int. Cl.² .................... C07D 213/26; A01N 9/22
[52] U.S. Cl. ........................................ 71/94; 546/294; 546/295; 546/296; 546/302
[58] Field of Search ............... 546/295, 294, 302, 296; 71/94

[56] References Cited

U.S. PATENT DOCUMENTS

| | | | |
|---|---|---|---|
| 2,922,790 | 1/1960 | Rockett et al. | 546/294 |
| 3,107,994 | 10/1963 | Rawlings et al. | 71/94 |
| 3,960,542 | 6/1976 | Plant et al. | 71/94 |

*Primary Examiner*—Alan L. Rotman

[57] ABSTRACT

Pyridine, 1-oxides, particularly 4- or 5-substituted pyridine, 1-oxides such as 2-[(1,1,2,2-tetrafluoroethyl)sulfinyl]pyridine, 1-oxide exhibit selective pre-emergence control of weeds.

18 Claims, No Drawings

HERBICIDAL PYRIDINE, 1-OXIDES

BACKGROUND OF THE INVENTION

This invention relates to herbicidal pyridine, 1-oxides, and, more particularly, to 4- or 5-substituted pyridine, 1-oxides which exhibit selective pre-emergence control of weeds in certain crops such as sugarbeets, peas and tobacco.

U.S. Pat. No. 4,050,921 discloses 2-alkyl sulphinyl and 2-alkylsulphonylpyridine, N-oxides of the formula

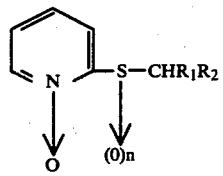

wherein
$R_1$ is hydrogen, alkyl, Ph or PhCH$_2$;
$R_2$ is hydrogen, alkyl, alkenyl, alkoxycarbonyl, among others; and
n is 1 or 2
and teaches their use as plant growth regulants.

U.S. Pat. No. 3,295,946 discloses compounds such as 2-(2,3,6-trichlorobenzylthio)pyridine, 1-oxide and 2-(polychlorobenzylthio)pyridine, 1-oxide and teaches a method of controlling vegetation which comprises applying thereto a phytotoxic concentration of such benzylthiopyridine oxides.

Neither reference indicates that the 4- or 5-substituted pyridine, 1-oxides of this invention would exhibit selective pre-emergence control of weeds.

SUMMARY OF THE INVENTION

The present invention relates to compounds, compositions containing them as active ingredient and a method of controlling undesirable vegetation utilizing such compounds of the Formula (I)

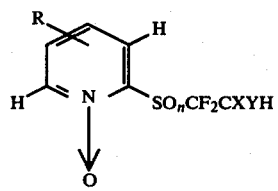

wherein
R is hydrogen, fluorine, bromine, chlorine, alkyl of 1 to 4 carbon atoms, CF$_3$, OCH$_3$ or OCF$_2$CXYH;
X is fluorine, bromine or chlorine;
Y is fluorine, bromine or chlorine; and
n is 0, 1 or 2.
provided that when n is 0 or 2, then R is hydrogen or methyl, X is fluorine or chlorine and Y is fluorine.

Preferred for their favorable cost and herbicidal activity are those compounds of Formula (I) where R is hydrogen, chlorine, bromine or methyl, X is fluorine or chlorine, Y is fluorine and n is 1.

More preferred on the basis of their higher herbicidal activity are those compounds of Formula (I) where R is hydrogen or methyl, X is fluorine or chlorine, Y is fluorine and n is 1.

Most preferred for their excellent herbicidal activity and favorable cost are 2-[(1,1,2,2-tetrafluoroethyl)sulfinyl]pyridine, 1-oxide and 2-[(2-chloro-1,1,2-trifluoroethyl)sulfinyl]pyridine, 1-oxide and 4-methyl-2[(1,1,2,2-tetrafluoroethyl)sulfinyl]pyridine, 1-oxide.

DETAILED DESCRIPTION OF THE INVENTION

Preparation

The compounds of this invention can be prepared as shown in the following reaction sequence:

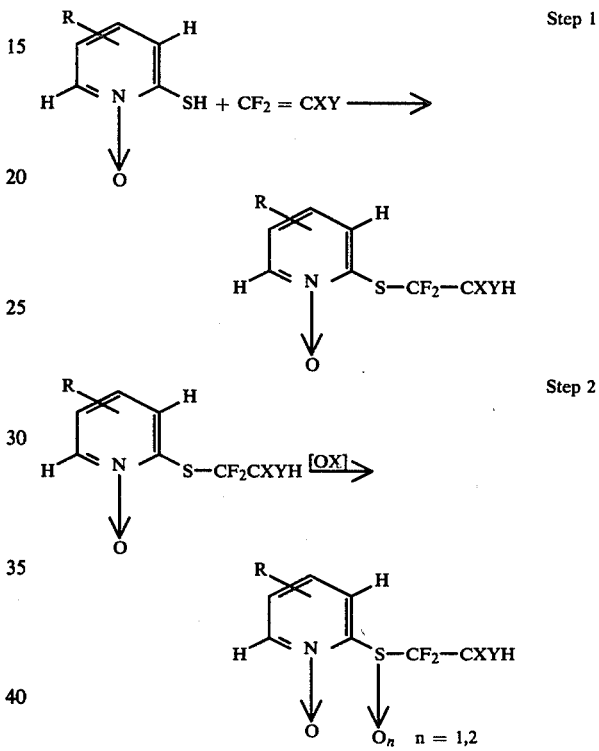

Step 1
The preparation of 2-pyridinethiol, 1-oxide is known, e.g. M. Nakanishi, S. Saheki, K. Iimori, Japan 72-40,052, CA, 77, 164494e (1972); Japan 72-40,057, CA 78, 41316 (1973) Japan 74-34,809, CA 83, 2371 j (1975) and E. F. Elslager, D. F. Worth Ger. Offen. 2,407,937, CA 81, 169532h (1974). The reaction of the 2-pyridinethiol, 1-oxides with difluorodihaloethylenes takes place normally at 0° to 50° C., preferably under autogenous pressure, in a solvent such as dimethylformamide in the presence of a basic catalyst such as diisopropylamine to produce the 2-[(1,1-difluoro-2,2-dihaloethyl)thio]pyridine, 1-oxides.

Step 2
The oxidation of the 2-[(1,1-difluoro-2,2 dihaloethyl)thio]pyridine, 1-oxides proceeds with an oxidizing agent such as m-chloroperoxybenzoic acid in an inert solvent such as methylene chloride at a temperature of from about 0° to 30° C. to produce the 2-[(1,1-difluoro-2,2-dihaloethyl)sulfinyl]pyridine, 1-oxides. More stringent oxidation conditions using additional oxidizing agent, such as m-chloroperoxybenzoic acid, and higher temperatures, such as in refluxing chloroform, i.e., about 60° to 80° C., produce the 2-[(1,1-difluoro-2,2 dihaloethyl)sulfonyl]pyridine, 1-oxides.

The following examples further illustrate the preparation of the compounds of this invention.

EXAMPLE 1

A mixture of 42 grams of 2-pyridinethiol, 1-oxide, 150 ml of dimethylformamide and 36 grams of diisopropylamine in a stainless steel pressure vessel was pressurized with 4.95 grams of tetrafluoroethylene at −20° C. and heated to 50° C. for 6 hours with rocking. After cooling to ambient temperature, the pressure vessel was vented and the resulting reaction solution was poured into 300 ml of ice water. The aqueous reaction mixture was extracted four times, using 300 ml of diethyl ether each time. The combined diethyl ether extracts were washed three times, using 500 ml of cold water each time. After washing the diethyl ether solution once with 500 ml of saturated aqueous sodium chloride solution, the diethyl ether solution was dried over 100 grams of anhydrous sodium sulfate and evaporated under reduced pressure of 300 mm Hg to 49.6 grams of a semisolid. The semisolid was crystallized from 1-chlorobutane to yield 31 grams of 2-(1,1,2,2-tetrafluoroethylthio)pyridine, 1-oxide melting 67.5°–68.5° C.

The following compounds can be prepared by replacing tetrafluoroethylene with chlorotrifluoroethylene, bromotrifluoroethylene, 1,1-dichloro-2,2-difluoroethylene or 1,1-dibromo-2,2-difluoroethylene in Example I:

2-(2-chloro-1,1,2-trifluoroethylthio)pyridine, 1-oxide, oil.

2-(2-bromo-1,1,2-trifluoroethylthio)pyridine, 1-oxide, oil, $n_D^{25}$ 1.5670.

2-(2,2-dichloro-1,1-difluoroethylthio)pyridine, 1-oxide, oil $n_D^{25}$ 1.5385

2-(2,2-dibromo-1,1-difluoroethylthio)pyridine, 1-oxide,

The following compounds can be prepared by replacing the appropriately substituted 2-pyridinethiol, 1-oxide for 2-pyridinethiol, 1-oxide in Example I:

5-bromo-2-(1,1,2,2-tetrafluoroethylthio)pyridine, 1-oxide 4-methyl-2-(1,1,2,2-tetrafluoroethylthio)pyridine, 1-oxide 5-butyl-2-(1,1,2,2-tetrafluoroethylthio)pyridine, 1-oxide 5-trifluoromethyl-2-(1,1,2,2-tetrafluoroethyl thio)pyridine, 1-oxide, oil, $n_D^{25}$ 1.4348

4-methoxy-2-(1,1,2,2-tetrafluoroethylthio)pyridine, 1-oxide 5-(1,1,2,2-tetrafluoroethoxy)-2-(1,1,2,2-tetrafluoroethylthio)pyridine, 1-oxide 5-fluoro-2-(1,1,2,2-tetrafluoroethylthio)pyridine, 1-oxide 5-chloro-2-(1,1,2,2-tetrafluoroethylthio)pyridine, 1-oxide.

EXAMPLE 2

To a solution of 10 grams of 2-(1,1,2,2-tetrafluoroethylthio)pyridine, 1-oxide in 100 ml of methylene chloride, 9.1 grams of 85% pure m-chloroperoxybenzoic acid was added in 5 equal portions over a 10 min. period with stirring. The reaction mixture was allowed to warm to ambient temperature during two hours and was stirred for 48 hours at ambient temperature. The resulting slurry was filtered of m-chlorobenzoic acid and the precipitate washed with 50 ml methylene chloride. The filtrate and wash were combined and washed sequentially with 100 grams of cold water and 100 grams of 5% aqueous sodium sulfite solution. The methylene chloride solution was dried over 20 grams of anhydrous sodium sulfate and evaporated under reduced pressure to 8.2 grams of beige crystals. After recrystallizing from 20 grams of 1-chlorobutane, 4.9 grams of 2-(1,1,2,2-tetrafluorothysulfinyl)pyridine, 1-oxide were isolated as beige crystals melting 109°–111° C.

The following compounds can be prepared by replacing 2-(1,1,2,2-tetrafluoroethylthio)pyridine, 1-oxide with the appropriately substituted 2-ethylthiopyridine, 1-oxide in Example 2:

2-(2-chloro-1,1,2-trifluoroethylsulfinyl)pyridine, 1-oxide m.p. 102°–110° C.

2-(2,2-dichloro-1,1-difluoroethylsulfinyl)pyridine, 1-oxide, oil, $n_D^{25}$: 1.5463

4-methyl-2-(1,1,2,2-tetrafluoroethylsulfinyl)pyridine, 1-oxide m.p. 91°–103° C.

5-trifluoromethyl-2-(1,1,2,2-tetrafluoroethylsulfinyl)pyridine, 1-oxide 5-bromo-2-(1,1,2,2-tetrafluoroethylsulfinyl) pyridine, 1-oxide m.p. 136°–142° C.

2-(2-bromo-1,1,2-trifluoroethylsulfinyl)pyridine, 1-oxide 2-(2,2-dibromo-1,1-difluoroethylsulfinyl)pyridine, 1-oxide 5-butyl-2-(1,1,2,2-tetrafluoroethylsulfinyl) pyridine, 1-oxide 4-methoxy-2-(1,1,2,2-tetrafluoroethylsulfinyl) pyridine, 1-oxide 5-(1,1,2,2-tetrafluoroethoxy)-2-(1,1,2,2-tetrafluoroethylsulfinyl)pyridine, 1-oxide 5-fluoro-2-(1,1,2,2-tetrafluoroethylsulfinyl) pyridine, 1-oxide 5-chloro-2-(1,1,2,2-tetrafluoroethylsulfinyl) pyridine, 1-oxide

EXAMPLE 3

To a solution of 10 grams of 2-(1,1,2,2-tetrafluoroethylthio)pyridine, 1-oxide in 150 ml of chloroform, 18.3 grams of 85% pure m-chloroperoxybenzoic acid was added in 4 portions over 15 min. at ambient temperature. After stirring for 16 hours at ambient temperature, the mixture was refluxed for 7 days. A 6 gram portion of m-chloroperoxybenzoic acid was added and the reaction mixture refluxed 3 days. The reaction mixture was diluted to 500 ml with chloroform and stirred for 3 days in the presence of 100 grams of anhydrous potassium carbonate. The slurry was filtered and the filtrate evaporated under reduced pressure of 300 mm Hg to 12.2 grams of a light yellow oil which slowly crystallized. The product was recrystallized from 50 ml of 1-chlorobutane to yield 5.2 grams of white 2-(1,1,2,2-tetrafluoroethylsulfonyl)pyridine, 1-oxide melting 60°–68° C.

The following compounds can be prepared by replacing 2-(1,1,2,2-tetrafluoroethylthio)pyridine, 1-oxide with 2-(2-chloro-1,1,2-trifluoroethylthio)pyridine, 1-oxide and 4-methyl-2-(1,1,2,2-tetrafluoroethylsulfonyl)pyridine, 1-oxide in Example 3:

2-(2-chloro-1,1,2-trifluoroethylsulfonyl)pyridine, 1-oxide 4-methyl-2-(1,1,2,2-tetrafluoroethylsulfonyl)pyridine, 1-oxide.

Formulations

Useful formulations of the compounds of Formula I can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table 1.

Table 1

|  | Weight Percent* | | |
| --- | --- | --- | --- |
|  | Active Ingredient | Diluent(s) | Surfactant(s) |
| Wettable Powders | 20-90 | 0-74 | 1-10 |
| Oil Suspensions, Emulsions (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active Ingredient plus at least one of a Surfactant or a Diluent equals 100 weight percent.

Lower or higher levels of active ingredient can be present, depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

Solutions ordinarily are prepared by simply mixing the ingredients. Fine solid compositions can be made by blending, and usually grinding, as in a hammer or fluid energy mill. Suspensions are usually prepared by wet milling (see, for example, Littler, U.S. Pat. No. 3,060,084). Granules and pellets can be made by spraying the active material on preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

The following examples further illustrate this invention. Unless indicated otherwise, all parts are by weight.

EXAMPLE 4

Wettable Powder

| | |
| --- | --- |
| 2-[(1,1,2,2-tetrafluoroethyl)sulfinyl]pyridine, 1-oxide | 50% |
| sodium alkylnaphthalenesulfonate | 2% |
| low viscosity methyl cellulose | 2% |
| diatomaceous earth | 46% |

The ingredients are blended, coarsely hammer-milled and then air milled to produce particles essentially all below 10 microns in diameter. The product is reblended before packaging.

EXAMPLE 5

Granule

| | |
| --- | --- |
| Wettable powder of Example (4) | 10% |
| attapulgite granules (low volative matter, 0.71/0.30 mm; U.S.S. 25-50 sieves) | 90% |

A slurry of wettable powder containing ≈25% solids is sprayed on the surface of attapulgite granules in a double-cone blender. The granules are dried and packaged.

EXAMPLE 6

Emulsifiable Concentrate

| | |
| --- | --- |
| 2-[(2-chloro-1,1,2-trifluoroethyl)sulfinyl]pyridine, 1-oxide | 30% |
| blend of oil soluble sulfonates and polyoxyethylene ethers | 4% |
| cyclohexanone | 66% |

The ingredients are combined and stirred with gentle warming to speed solution. A fine screen filter is included in the packaging operation to insure the absence of any extraneous undissolved material in the product.

EXAMPLE 7

Solution

| | |
| --- | --- |
| 2-[(2-chloro-1,1,2-trifluoroethyl)sulfinyl]pyridine, 1-oxide | 50% |
| dimethylformamide | 50% |

The ingredients are stirred together with slight warming to speed solution to make a solution for direct low-volume application.

Utility

The compounds of this invention are useful for the pre-emergence control of weeds in certain crops, such as sugarbeets, peas and tobacco.

The precise amount of the compounds of this invention to be used in any particular situation will vary depending on such factors as the plant species to be controlled, soil type, formulation used, irrigation practices followed, length of time for which residual control is desired, etc. Broadly speaking, the compounds are used at levels of about 0.06 to 5 kilograms per hectare, preferably in the range of about 0.12 to 3 kilograms per hectare.

The compounds of this invention may be used in combination with any other commercial herbicide such as the triazine, triazole, uracil, urea, amide and diphenylether types.

The herbicidal properties of the subject compounds were discovered in a number of greenhouse and field tests, as described hereinafter.

EXAMPLE 8

Seeds of crabgrass (Digitaria spp.), barnyardgrass (*Echinochloa crusgalli*), wild oats (*Avena fatua*), Cassia tora, morningglory (Ipomoea spp.), cocklebur (Xanthium spp.), sorghum, corn, soybean, rice, wheat as well as nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three-five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings: B=burn; G=growth retardation; C=chlorosis/necrosis; D=defoliation, 6Y=abscised buds or flowers, 6F=delayed flowering, E=emergence inhibition; and H=formative effects. The ratings for the compounds tested by this procedure are presented in Table 2.

Table #2

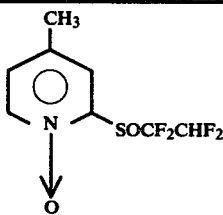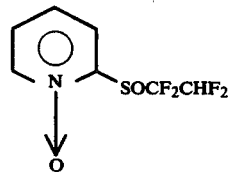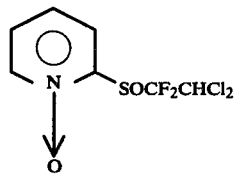

| kg/ha | 2 | 2 | 2 |
| --- | --- | --- | --- |
| POST EMERGENCE | | | |
| BUSH BEAN | 2H, 6Y | 1B, 6H, 6Y | — |
| COTTON | 5B, 3D | 3B, 8G | — |
| MORNING GLORY | 1B | 3B, 6G | 0 |
| COCKLEBUR | 1B | 9C | 0 |
| CASSIA | 1B | 5G | 0 |
| NUTSEDGE | 8G | 6G | 2G |
| CRABGRASS | 3C, 9G | 1B, 7G | 5C, 9H |
| BARNYARD GRASS | 5C, 9H | 1B, 9H | 9H |
| WILD OATS | 9H | 1B, 7G | 0 |
| WHEAT | 9G | 1B, 3G | 0 |
| CORN | 9H | 9H | 8H |
| SOYBEAN | 5H | 1B, 6H | 1H |
| RICE | 9G | 1B, 7G | 3G |
| SORGHUM | 9H | 1B, 8G | 3G |
| PRE EMERGENCE | | | |
| MORNING GLORY | 6H | 1C, 8G | 1C |
| COCKLEBUR | 7H | 1C, 5G | 1C, 5G |
| CASSIA | 6G | 8G | 2C |
| NUTSEDGE | 10E | 10E | 9G |
| CRABGRASS | 10H | 10E | 10E |
| BARNYARD GRASS | 10H | 10H | 10H |
| WILD OATS | 9H | 9H | 9H |
| WHEAT | 10H | 9H | 10H |
| CORN | 10H | 9H | 9H |
| SOYBEAN | 9H | 9H | 3H |
| RICE | 10E | 10E | 10E |
| SORGHUM | 10H | 10H | 10H |

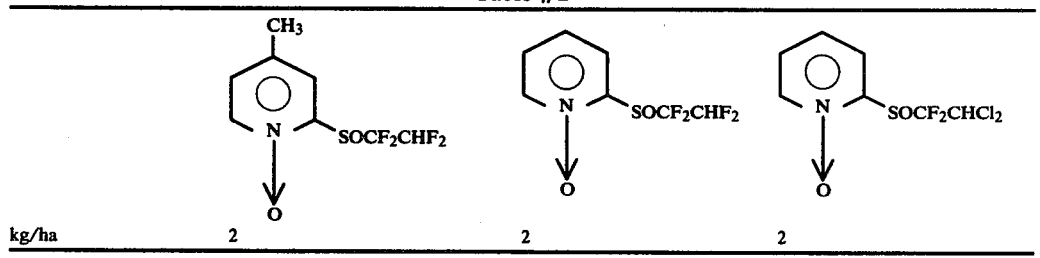

| kg/ha | 2 | 2 | 2 |
| --- | --- | --- | --- |
| POST EMERGENCE | | | |
| BUSH BEAN | 1B, 7G, 6Y | 2B | 2H |
| COTTON | 1B, 6G | 2B, 7H | 0 |
| MORNING GLORY | 1B, 7G | 2B, 6H | 0 |
| COCKLEBUR | 0 | 2B | 6F |
| CASSIA | 0 | 1B, 2H | 0 |
| NUTSEDGE | 5G | 8G | 0 |
| CRABGRASS | 1B, 8G | 2B, 9G | 1C, 9G |
| BARNYARD GRASS | 1B, 9H | 2B, 9H | 9H |
| WILD OATS | 9H | 9H | 0 |

Table #2-continued

| | | | |
|---|---|---|---|
| WHEAT | 8G | 9G | 0 |
| CORN | 9H | 9H | 2G |
| SOYBEAN | 4H | 1B, 7H | 1B, 1H |
| RICE | 1B, 8G | 1B, 9G | 9G |
| SORGHUM | 1B, 9G | 1B, 9H | 9H |
| PRE EMERGENCE | | | |
| MORNING GLORY | 2G | 8H | 0 |
| COCKLEBUR | 2G | 7H | 0 |
| CASSIA | 0 | 9G | 0 |
| NUTSEDGE | 6G | 10E | 9G |
| CRABGRASS | 10E | 10E | 10H |
| BARNYARD GRASS | 10H | 10E | 10H |
| WILD OATS | 9H | 10E | 8H |
| WHEAT | 9H | 10E | 7H |
| CORN | 9H | 10H | 9H |
| SOYBEAN | 5G | 9H | 2G |
| RICE | 10E | 10E | 10E |
| SORGHUM | 10H | 10H | 9H |

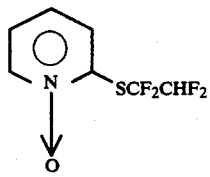 SCF₂CHF₂

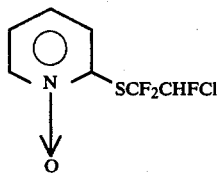 SCF₂CHFCl

| kg/ha | 2 | 2 |
|---|---|---|
| POST EMERGENCE | | |
| BUSH BEAN | 1H | 1B, 2H |
| COTTON | 3B | 4B, 2H |
| MORNING GLORY | 2C, 7G | 1B |
| COCKLEBUR | 0 | 1B |
| CASSIA | 1B | 1B, 3H |
| NUTSEDGE | 0 | 0 |
| CRABGRASS | 4H | 1B, 6H |
| BARNYARD GRASS | 0 | 1B |
| WILD OATS | 0 | 1B |
| WHEAT | 0 | 1B |
| CORN | 1H | 1B, 3G |
| SOYBEAN | 1B | 0 |
| RICE | 0 | 1B, 8G |
| SORGHUM | 1B, 7G | 2B, 8G |
| PRE EMERGENCE | | |
| MORNING GLORY | 0 | 1C |
| COCKLEBUR | 0 | 0 |
| CASSIA | 1C | 0 |
| NUTSEDGE | 10E | 10E |
| CRABGRASS | 8H | 9H |
| BARNYARD GRASS | 9H | 9H |
| WILD OATS | 9H | 9H |
| WHEAT | 9H | 9H |
| CORN | 9H | 9H |
| SOYBEAN | 9H | 7H |
| RICE | 2G | 9H |
| SORGHUM | 10E | 10H |

EXAMPLE 9

Two plastic bulb pans were filled with fertilized and limed Fallsington silt loam. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats ((*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassis (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated preemergence with several test compounds within the scope of the invention.

Twenty-eight days after treatment, the plants were evaluated and visually rated for response to the chemical treatments utilizing the rating system described previously for Example 8. The data are summarized in Table 3. Certain compounds exhibit selective pre-emergence weed control in crops such as soybeans and sugarbeets.

Table 3

Preemergence on Fallsington Silt Loam

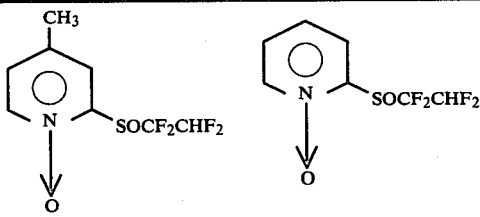

| Rate, kg/ha | 0.06, | 0.12, | 0.50 | 0.06, | 0.06, | 0.12, | 0.25, | 1.00 |
|---|---|---|---|---|---|---|---|---|
| CRABGRASS | 9H | 10H | 10E | 9H | 0 | 10H | 10H | 10H |
| BARNYARDGRASS | 10H | 10H | 10H | 8H | 7H | 9H | 9H | 10H |
| SORGHUM | 9H | 10H | 10H | 5H | 3G | 5H | 10H | 10H |
| WILD OATS | 10H | 9H | 10H | 3H | 0 | 4H | 8H | 10H |
| JOHNSONGRASS | 9H | 9H | 10H | 3H | 0 | 8H | 10H | 10H |
| DALLISGRASS | 9H | 10H | 10E | 5H | 0 | 7H | 10H | 10H |
| GIANT FOXTAIL | 10H | 10H | 10H | 10H | 0 | 3H | 10H | 10H |
| KY. BLUEGRASS | 10H | 10E | 10E | 4H | 0 | 0 | 10E | 10E |
| CHEATGRASS | 10H | 10E | 10E | 10H | 0 | 4H | 10H | 10H |
| SUGARBEETS | 0 | 0 | 3G | 0 | 0 | 0 | 0 | 5H |
| CORN | 9H | 10H | 10H | 8H | 0 | 9H | 9H | 10H |
| MUSTARD | 0 | 0 | 10C | 0 | 0 | 4G | 4G | 7H |
| COCKLEBUR | 0 | 0 | 0 | 0 | — | 0 | 0 | 3H |
| PIGWEED | 10C | 10C | 10C | 3C | 0 | 3G | 10E | 10E |
| NUTSEDGE | 4G | 6G | 7G | 0 | 0 | 0 | 9G | 10E |
| COTTON | 0 | 0 | 4H | 0 | — | — | — | — |
| MORNINGGLORY | 0 | 0 | 0 | — | 0 | 0 | 3H | 6H |
| CASSIA | 0 | 0 | 3G | 0 | 0 | 0 | 4H | 10E |
| TEAWEED | 0 | 9C | 10C | 0 | — | — | — | — |
| VELVETLEAF | — | 0 | 0 | 0 | 0 | 0 | 0 | 3H |
| JIMSONWEED | 0 | 0 | 8C | 0 | 0 | 0 | 0 | 10H |
| SOYBEAN | 0 | 2H | 6H | 0 | 0 | 0 | 0 | 9H |
| RICE | 9H | 10H | 10E | 7H | 0 | 7H | 9H | 10E |
| WHEAT | 6H | 10H | 10E | 3H | 0 | 7H | 9H | 10E |

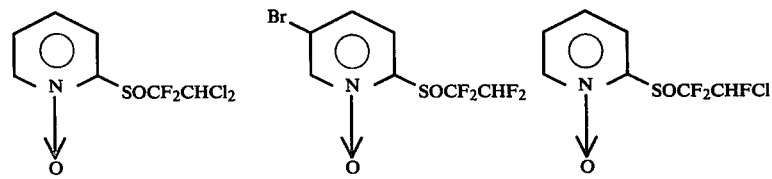

| Rate, kg/ha | 0.12, | 0.50 | 0.12, | 0.50 | 0.06, | 0.12, | 0.50 |
|---|---|---|---|---|---|---|---|
| CRABGRASS | 9H | 10E | 10E | 10E | 9H | 10E | 10E |
| BARNYARDGRASS | 0 | 6H | 9H | 10H | 10H | 10H | 10H |
| SORGHUM | 0 | 0 | 10H | 10H | 6H | 7H | 10H |
| WILD OATS | 0 | 3H | 3H | 9H | 6H | 7H | 10H |
| JOHNSONGRASS | 0 | 4H | 9H | 10E | 8H | 9H | 10H |
| DALLISGRASS | 0 | 6H | 9H | 9H | 7H | 10H | 10H |
| GIANT FOXTAIL | 4H | 10H | 10H | 10E | 9H | 10H | 10H |
| KY. BLUEGRASS | 0 | 3H | 10E | 10E | 10H | 10E | 10E |
| CHEATGRASS | 0 | 10E | 10H | 10E | 9H | 10E | 10E |
| SUGARBEETS | 0 | 0 | 0 | 4G | 0 | 0 | 0 |
| CORN | 0 | 0 | 3H | 7H | 4H | 7H | 10H |
| MUSTARD | 0 | 0 | 0 | 7G | 0 | 0 | 3C |
| COCKLEBUR | 0 | 0 | — | 0 | 0 | 0 | — |
| PIGWEED | 0 | 5C | 10E | 10E | 0 | 9C | 10E |
| NUTSEDGE | 0 | 0 | 0 | 5G | 0 | 8G | 10E |
| COTTON | 0 | 0 | 6G | 7G | 0 | 2G | 7G |
| MORNINGGLORY | 0 | 0 | 0 | 0 | — | 0 | 5G |
| CASSIA | 0 | 0 | 0 | 0 | 0 | 0 | 5G |
| TEAWEED | 0 | 0 | 0 | 10C | — | 0 | 0 |
| VELVETLEAF | — | 0 | 7G | 10C | 0 | 0 | 7G |
| JIMSONWEED | 0 | 0 | 0 | 0 | 0 | 0 | 3G |
| SOYBEAN | 0 | 2G | 2G | 3G | 0 | 0 | 4G,5H |
| RICE | 0 | 10E | 5C | 10C | 9H | 9H | 10E |
| WHEAT | 0 | 4H | 0 | 2H | 3H | 9H | 10E |

Table 3-continued

| | Preemergence on Fallsington Silt Loam | | | |
|---|---|---|---|---|
| | 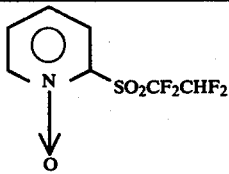 $SO_2CF_2CHF_2$ | | 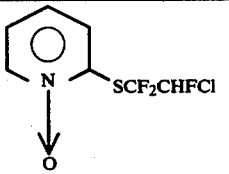 $SCF_2CHFCl$ | |
| Rate, kg/ha | 0.12, | 0.50 | 0.12, | 0.50 |
| CRABGRASS | 10E | 10E | 0 | 0 |
| BARNYARDGRASS | 9H | 10H | 0 | 0 |
| SORGHUM | 5G | 5H | 0 | 10H |
| WILD OATS | 0 | 0 | 0 | 0 |
| JOHNSONGRASS | 10C | 9H | 0 | 10H |
| DALLISGRASS | 10H | 10H | 0 | 6H |
| GIANT FOXTAIL | 8H | 10H | 10H | 10H |
| KY. BLUEGRASS | 8H | 10E | 0 | 0 |
| CHEATGRASS | 0 | 6H | 0 | 0 |
| SUGARBEETS | 0 | 0 | 0 | 0 |
| CORN | 0 | 4G | 0 | 0 |
| MUSTARD | 0 | 0 | 0 | 3C |
| COCKLEBUR | 0 | 0 | 0 | 0 |
| PIGWEED | 0 | 10E | 0 | 0 |
| NUTSEDGE | 0 | 0 | 0 | 0 |
| COTTON | 0 | 0 | 0 | 0 |
| MORNINGGLORY | 0 | 0 | 0 | 0 |
| CASSIA | 0 | 0 | 0 | 0 |
| TEAWEED | 0 | 0 | 0 | 0 |
| VELVETLEAF | 0 | 6G | 0 | 0 |
| JIMSONWEED | 0 | 0 | 0 | 0 |
| SOYBEAN | 0 | 0 | 0 | 0 |
| RICE | 3H | 6H | 0 | 0 |
| WHEAT | 0 | 0 | 0 | 0 |

EXAMPLE 10

Twenty-five cm diameter plastic pots filled with Fallsington silt loam were planted to soybeans, cotton, alfalfa, corn, rice wheat, sorghum, velvetleaf (*Abutilon theophrasti*), Cassia (*Cassia tora*), morningglory (*Ipomoea hederacea*), jimsonweed (*Datura stramonium*), cocklebur (*Xanthium pennsylvanicum*), crabgrass (*Digitaria* spp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a non-phytotoxic solvent. Fourteen days after treatment, all species were compared to untreated controls and visually rated for response to treatment. The rating system was as described previously for Example 8. The data are presented in Table 4. Several of the compounds tested by this procedure exhibited selective post-emergence control of weeds in wheat.

Table 4

| | Over-the-Top Soil/Foliage Treatment | | | | |
|---|---|---|---|---|---|
| | 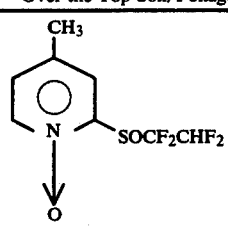 $SOCF_2CHF_2$ | | 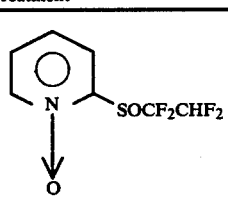 $SOCF_2CHF_2$ | | |
| Rate, kg/ha | 0.12, | 0.50 | 0.12, | 0.25, | 1.00 |
| SOYBEANS | 4H | 6H | 3H | 3G, 2H | 5G, 3H |
| VELVETLEAF | 0 | 0 | 0 | 3G, 3H | — |
| SESBANIA | 0 | 2C | 0 | 4C | 8C |
| CASSIA | 0 | 0 | 0 | 3C | 3C |
| COTTON | 0 | 2H | 0 | 0 | 3H |
| MORNINGGLORY | 0 | 0 | 0 | 0 | 3H |
| ALFALFA | 0 | 3G | 0 | 0 | 2H |
| JIMSONWEED | 0 | 6C | 0 | 2H | 4H |
| COCKLEBUR | 0 | 0 | 0 | 2H | 2H |
| CORN | 5H | 5H | 2H | 3G | 6H |
| CRABGRASS | 5H, 2C | 5H, 7C | 2H | 5H | 7H |
| RICE | 3G | 10G | 2G | 4H | 4H |
| NUTSEDGE | 0 | 0 | 0 | — | 4G |
| BARNYARDGRASS | 6H | 6H | 4H | 3H | 5H |
| WHEAT | 0 | 5G | 0 | 3H | 5H |
| GIANT FOXTAIL | 8G,3H | 10G,5H | 5G,3H | 5H | 8H |
| WILD OATS | 5G | 7G | 0 | 2H | 5H |
| SORGHUM | 3G | 7H | 3G | 2H | 4H |

Table 4-continued

Over-the-Top Soil/Foliage Treatment

| | Br–⟨pyridine N→O⟩–SOCF$_2$CHF$_2$ | | ⟨pyridine N→O⟩–SOCF$_2$CHFCl | | |
|---|---|---|---|---|---|
| Rate, kg/ha | 0.25, | 1.00 | 0.12, | 0.12, | 0.50 |
| SOYBEANS | 0 | 3H | 4H | 3H | 6H |
| VELVETLEAF | 0 | 0 | — | 0 | 0 |
| SESBANIA | 0 | 0 | 0 | 0 | 0 |
| CASSIA | 0 | 0 | 0 | 0 | 5G |
| COTTON | 0 | 2H | 0 | 0 | 3H |
| MORNINGGLORY | 0 | 4G | 0 | 0 | 4C |
| ALFALFA | 0 | 0 | 0 | 0 | 4G |
| JIMSONWEED | 0 | 0 | 0 | 3C | 0 |
| COCKLEBUR | 0 | 0 | 0 | 2C | 2C |
| CORN | 0 | 7H | 3H | 3G | 5H |
| CRABGRASS | 5H | 10H | 5H | 5H | 8H |
| RICE | 3H | 6H | 0 | 0 | 5H |
| NUTSEDGE | 0 | 3G | 0 | 0 | 3H |
| BARNYARDGRASS | 4H | 5H | 4H | 5H | 8H |
| WHEAT | 2G | 4G | 0 | 2G | 4G |
| GIANT FOXTAIL | 5H | 8H | 8G,3H | 6H | 7H |
| WILD OATS | 6H | 6H | 5G | 2H | 5H |
| SORGHUM | 4H | 7H | 2G | 0 | 6H |

EXAMPLE 11

A number of plastic bulb pans were filled with fertilized and limed Fallsington silt loam. One set of pans was planted to the following weed species whose seeds were uniformly mixed with the top 3.7 cm layer of soil: johnsongrass (*Sorghum halepense*), barnyardgrass (*Echinochloa crusgalli*), crabgrass (*Digitaria sanguinalis*), giant foxtail (*Setaria faberii*), velvetleaf (*Abutilon theophrasti*), jimsonweed (*Datura stramonium*), mustard (*Brassica arvensis*) and pigweed (*Amaranthus retroflexus*). Another set of pans was planted to the following crops, from one to four different species per pan and with the planting depth indicated in parentheses: corn (3.7 cm), cotton (2.5 cm), soybeans (2.5 cm), sunflower (2.5 cm), oats (2.5 cm), wheat (2.5 cm), Black Valentine bean (2.5 cm), rice (2.5 cm), sorghum (2.5 cm), peas (2.5 cm), barley (2.5 cm), cucumbers (1.2 cm), cabbage (1.2 cm), alfalfa (1.2 cm), safflower (1.2 cm), sugarbeets (1.2 cm), tomato (1.2 cm), spinach (1.2 cm) and Kentucky bluegrass (1.2 cm). In addition, young tobacco plants were transplanted into 15 cm diameter plastic pots filled with the same soil.

One series of each of the crop plantings and one pot containing weed seeds were left untreated and served as controls. The remaining pots were treated pre-emergence at various rates of application with one of the test compounds within the scope of the invention. The one exception was tobacco, where the test compound was applied as a drench treatment on the surrounding soil surface. The plants were visually rated for response twenty-eight days after treatment utilizing the rating system described previously for Example 8. The data are given in Table 5.

The data indicate that the test compound has utility for the control of weeds in certain crops such as peas and tobacco.

Table 5

⟨pyridine N→O⟩–SOCF$_2$CHF$_2$

| Rate, kg/ha | 0.03, | 0.06, | 0.12, | 0.12, | 0.25, | 0.50, | 1.00 |
|---|---|---|---|---|---|---|---|
| CORN | — | — | — | — | 9C | 10C | 10C |
| COTTON | — | — | — | — | 7C | 8C | 9C |
| SOYBEAN | — | — | — | — | 4H | 7H | 9C |
| SUNFLOWER | — | — | — | — | — | — | 10C |
| OATS | — | — | — | — | — | — | 10C |
| WHEAT | — | — | — | — | 9H | 10H | 10E |
| SORGHUM | — | — | — | — | 9H | 10H | 10E |
| SUGAR BEET | — | — | — | — | 10C | 10C | 4H |
| PEA | — | — | — | — | 0 | 0 | 5C |
| ALFALFA | — | — | — | — | 4H | 8H | 7H |
| BEAN | — | — | — | — | 6H | 8H | 7H |
| SPINACH | — | — | — | — | 10C | 10C | 10C |
| CABBAGE | — | — | — | — | 6G | 9C | 10C |
| TOMATO | — | — | — | — | 10C | 10C | 10C |
| RICE | — | — | — | — | 10C | 10C | 10E |
| SAFFLOWER | — | — | — | — | — | — | 10C |
| CUCUMBER | — | — | — | — | 7G | 10C | 10C |
| KY. BLUEGR. | — | — | — | — | 10C | 10C | 10E |
| BARLEY | — | — | — | — | 10C | 10C | 10E |
| TOBACCO | — | — | — | — | 0 | 0 | — |
| BROADLEAVES | — | — | — | 0 | 2C | 3C | — |
| GRASSES | 4C | 8C | 10C | 10C | 10C | 10C | — |

EXAMPLE 12

This example demonstrates the high herbicidal activity of two of the compounds from within the scope of this invention when applied pre-emergence to soil. Containers used were 25-cm diameter plastic pots filled with fertilized and limed Fallsington silt loam. The top 2.5 cm layer of soil was uniformly infested with seeds of the following weed species: crabgrass (*Digitaria sanguinalis*), barnyardgrass (*Echinochloa crusgalli*), giant foxtail (*Setaria faberii*) and johnsongrass (*Sorghum halepense*). Immediately after planting the test compounds, dissolved in a non-phytotoxic solvent, were applied to the soil surfaces at rates of 0.03 and 0.06 kg/ha. There were two replications of each treatment. One pot was left untreated for the purpose of comparison.

Twenty-eight days after treatment a visual estimate was made of the percent weed control obtained. The data are presented in Table 6.

Table 6

Pre-emergence Grass Control on Fallsington Silt Loam
Ratings Made 28 Days After Treatmemt

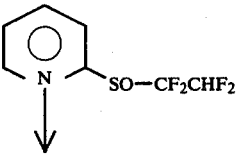

| Structure | Rate, kg/ha | Replicate | % Control Grasses[1] | |
|---|---|---|---|---|
| (top structure: pyridine N-oxide with SO—CF$_2$CHF$_2$) | 1/32 | A | 60 | 55 |
| | | B | 50 | |
| | 1/16 | A | 80 | 77 |
| | | B | 74 | |
| (bottom structure: pyridine N-oxide with SO—CF$_2$CHFCl) | 1/32 | A | 70 | 75 |
| | | B | 80 | |
| | 1/16 | A | 86 | 83 |
| | | B | 80 | |
| Untreated Check | — | — | 0 | |

[1] Crabgrass, barnyardgrass, giant foxtail, johnsongrass

EXAMPLE 13

Certain of the compounds within the scope of the present invention have utility for the pre-emergence control of grass weeds in sugarbeets.

Twenty-five centimeter diameter plastic pots filled with fertilized and limed Fallsington silt loam were planted to either sugarbeets (planting depth 1.2–1.7 cm), broadleaved weeds or grass weeds. The seeds of the weed species were mixed with the top 2.5 cm layer of soil. The broadleaved weeds used were: mustard (*Brassica arvensis*), velvetleaf (*Abutilon theophrasti*), jimsonweed (*Datura stramonium*), and pigweed (*Amaranthus retroflexus*); the grass weeds: crabgrass (*Digitaria sanguinalis*), giant foxtail (*Setaria faberii*) and barnyardgrass (*Echinochloa crusgalli*). Immediately after planting, the test compound, dissolved in a non-phytotoxic solvent, was applied at various rates as a pre-emergence treatment to the bare soil surfaces, leaving one pot each of sugarbeets, broadleaved weeds and grass weeds untreated as controls.

The plantings were maintained in a greenhouse for twenty-eight days and then visually rated for response to the treatments. The rating system used was as described for Example 8. Table 7 contains the results.

Table 7

Weed Control in Sugarbeets; Applied
Preemergence to Fallsington Silt Loam
Ratings made 28 Days after Treatment

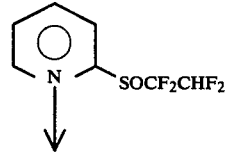

| Structure | Rate, (kg/ha) | Weed Control Broad-leaves[1] | Grasses[2] | Response Sugar-beets |
|---|---|---|---|---|
| (pyridine N-oxide with SOCF$_2$CHF$_2$) | 0.06 | 0 | 9C | |
| " | 0.12 | 2C | 9C+ | 0 |
| " | 0.25 | 3C | 10C | 0 |
| " | 0.50 | 5C | 10C | 2C |
| " | 1.0 | | | —[3] |
| " | 1.5 | | | —[3] |
| Untreated Check | — | 0 | 0 | 0 |

[1] Crabgrass, barnyardgrass, giant foxtail
[2] Mustard, velvetleaf, pigweed, jimsonweed
[3] Diseased

EXAMPLE 14

2-(1,1,2,2-tetrafluoroethylsulfinyl)pyridine, N-oxide was sprayed on freshly tilled and planted silt loam in plots 2 by 15 meters. Crops and weeds were planted across the plots on. Irrigation of about 1 inch was applied 4 days later. A heavy natural population of weeds was present (giant foxtail, ragweed and pigweed). Percent weed control and crop injury ratings were recorded 4 and/or 9 weeks after treatment. These are shown in Table 8 below.

Table 8

Preemergence Crop Tolerance and Weed Control Test.
Mean % Weed Control After 4 or 9 Weeks (Structure: pyridine N-oxide with SOCF$_2$CHF$_2$)

| | | Untreated | .25 | .5 | Kg ai/ha 1.0 | 2.0 |
|---|---|---|---|---|---|---|
| Grasses | 4 weeks | 0 | 80 | 87 | 95 | 99 |
| Grasses | 9 weeks | 0 | 25 | 60 | 93 | 97 |
| Broadleaves | 4 weeks | 0 | 50 | 65 | 50 | 45 |
| Broadleaves | 9 weeks | 0 | 15 | 15 | 0 | 0 |
| Crabgrass | 4 weeks | 0 | 50 | 70 | 90 | 100 |
| Foxtail | | 0 | 80 | 95 | 98 | 100 |
| Nutsedge | | 0 | 0 | 0 | 50 | 70 |
| Pigweed | | 0 | 100 | 100 | 100 | 100 |
| Ragweed | | 0 | 60 | 70 | 60 | 60 |
| Velvet Leaf | | 0 | 60 | 60 | 60 | 60 |
| Lambsquarter | | 0 | 80 | 80 | 80 | 80 |
| Purslane | | 0 | 60 | 60 | 60 | 90 |
| Smartweed | | 0 | 80 | 80 | 80 | 80 |
| Barnyard Grass | | 0 | 70 | 80 | 90 | 100 |
| Rye grass | | 0 | 30 | 60 | 90 | 100 |
| Wild Oats | | 0 | 0 | 20 | 70 | 90 |

Table 8-continued
Preemergence Crop Tolerance and Weed Control Test.
Mean % Weed Control After 4 or 9 Weeks

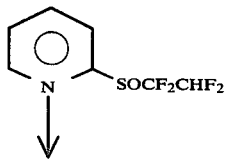

| | | Un-treated | .25 | .5 | Kg ai/ha 1.0 | 2.0 |
|---|---|---|---|---|---|---|
| Spinach | 4 weeks | 0 | — | — | 50 | 50 |
| Flax | | 0 | 0 | 0 | 0 | 10 |
| Endive | | 0 | 0 | 0 | 0 | 20 |
| Cabbage | | 0 | 0 | 0 | 0 | 0 |
| Red Beets | | 0 | — | — | — | — |
| Carrots | | 0 | 0 | 0 | 0 | 20 |
| Lima Beans | | 0 | 0 | 0 | 10 | 20 |
| Snap Beans | | 0 | 20 | 20 | 20 | 30 |
| Tomatoes | | 0 | 0 | 0 | 0 | 20 |
| Peanuts | | 0 | 0 | 0 | 0 | 0 |
| Potatoes | | 0 | 20 | 20 | 20 | 20 |
| Cucumbers | | 0 | 0 | 0 | 0 | 20 |
| Squash | | 0 | 0 | 0 | — | — |
| Sugarbeets | | 0 | — | — | — | — |
| Soybeans | | 0 | 0 | 0 | 20 | 20 |
| Alfalfa | | 0 | 0 | 0 | 0 | 0 |
| Clover | | 0 | 0 | 0 | 0 | 0 |
| Lespedeza | | 0 | 0 | 0 | 0 | 20 |
| Cotton | | 0 | 0 | 0 | 0 | 0 |
| Oats | | 0 | 0 | 0 | 20 | 70 |
| Okra | | 0 | 0 | 0 | 0 | 20 |
| Rice | | 0 | 0 | 0 | 50 | 100 |
| Wheat | | 0 | 0 | 0 | 20 | 70 |
| Sorghum | | 0 | 0 | 0 | 0 | 100 |
| Corn | | 0 | 0 | 0 | 90 | 100 |
| Sunflower | | 0 | 0 | 0 | 0 | 0 |
| Safflower | | 0 | 0 | 0 | 0 | 0 |

EXAMPLE 15

2-(1,1,2,2-tetrafluoroethylsulfinyl)pyridine N-oxide was sprayed pre-emergence on freshly tilled and planted Matapeake silt loam in 1 by 4 meter plots with 3 replications. Rainfall was recorded after 6 days (2 mm), 8 days (3 mm) and 9 days (23 mm). A heavy natural population of weeds was present. Percent weed control ratings were recorded 41 days after treatment and are shown in Table 9 below.

Table 9
Pre-emergence weed control in sugarbeets.
Mean % weed control and sugarbeet injury after 6 weeks.

| Material | kg/ha | Pig-weed | Purs-lane | Giant Foxtail | %Beet Injury |
|---|---|---|---|---|---|
| 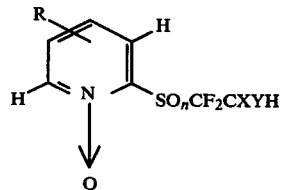 | .25 | 0 | 0 | 0 | 0 |
| | .5 | 10 | 0 | 47 | 0 |
| | 1.0 | 70 | 30 | 92 | 0 |
| | 2.0 | 60 | 58 | 99 | 0 |
| Hand Weeded check | — | 99 | 93 | 96 | 0 |
| Untreated check | — | 0 | 0 | 0 | 0 |
| Weeds per sq.ft. | | 1.3 | 2 | 3.3 | — |

What is claimed is:

1. A compound of the formula wherein
R is hydrogen, fluorine, bromine, chlorine, alkyl of 1 to 4 carbon atoms, $CF_3$, $OCH_3$ or $OCF_2CXYH$;
X is fluorine, bromine or chlorine;
Y is fluorine, bromine or chlorine; and n is 0, 1 or 2, provided that when n is 0 or 2, then R is hydrogen or methyl, X is fluorine or chlorine and Y is fluorine.

2. The compound as claimed in claim 1 wherein R is hydrogen, chlorine, bromine or methyl; X is fluorine or chlorine; Y is fluorine; and n is 1.

3. The compound as claimed in claim 1 wherein R is hydrogen or methyl; X is fluorine or chlorine, Y is fluorine; and n is 1.

4. The compound as claimed in claim 1 which is 2-(1,1,2,2-tetrafluoroethylsulfinyl)pyridine, 1-oxide.

5. The compound as claimed in claim 1 which is 2-(2-chloro-1,1,2-trifluoroethylsulfinyl) pyridine, 1-oxide.

6. The compound as claimed in claim 1 which is 4-methyl-2[(1,1,2,2-tetrafluoroethyl)sulfinyl]pyridine, 1-oxide.

7. A herbicidal composition consisting essentially of a herbicidally effective amount of a compound of claim 1 and at least one of (a) about 0.1% to 20% surfactant(s) and (b) about 1% to 99.9% solid or liquid diluent(s).

8. A herbicidal composition consisting essentially of a herbicidally effective amount of a compound of claim 2 and at least one of (a) about 0.1% to 20% surfactant(s) and (b) about 1% to 99.9% solid or liquid diluent(s).

9. A herbicidal composition consisting essentially of a herbicidally effective amount of a compound of claim 3 and at least one of (a) about 0.1% to 20% surfactant(s) and (b) about 1% to 99.9% solid or liquid diluent(s).

10. A herbicidal composition consisting essentially of a herbicidally effective amount of a compound of claim 4 and at least one of (a) about 0.1% to 20% surfactant(s) and (b) about 1% to 99.9% solid or liquid diluent(s).

11. A herbicidal composition consisting essentially of a herbicidally effective amount of a compound of claim 5 and at least one of (a) about 0.1% to 20% surfactant(s) and (b) about 1% to 99.9% solid or liquid diluent(s).

12. A herbicidal composition consisting essentially of a herbicidally effective amount of a compound of claim 6 and at least one of (a) about 0.1% to 20% surfactant(s) and (b) about 1% to 99.9% solid or liquid diluent(s).

13. A method for controlling weeds which comprises applying to said weeds a herbicidally effective amount of a compound of claim 1.

14. A method for controlling weeds which comprises applying to said weeds a herbicidally effective amount of a compound of claim 2.

15. A method for controlling weeds which comprises applying to said weeds a herbicidally effective amount of a compound of claim 3.

16. A method for controlling weeds which comprises applying to said weeds a herbicidally effective amount of a compound of claim 4.

17. A method for controlling weeds which comprises applying to said weeds a herbicidally effective amount of a compound of claim 5.

18. A method for controlling weeds which comprises applying to said weeds a herbicidally effective amount of a compound of claim 6.

* * * * *